US012678560B2

(12) United States Patent
Freitag et al.

(10) Patent No.: US 12,678,560 B2
(45) Date of Patent: *Jul. 14, 2026

(54) INJECTION MOLDED CANNULA SYSTEM

(71) Applicant: Roche Diabetes Care, Inc., Indianapolis, IN (US)

(72) Inventors: Christian Freitag, Weinolsheim (DE); Mads Bjoern Rasmussen, Weinheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 748 days.

This patent is subject to a terminal disclaimer.

(21) Appl. No.: 17/571,181

(22) Filed: Jan. 7, 2022

(65) Prior Publication Data

US 2022/0126019 A1 Apr. 28, 2022

Related U.S. Application Data

(63) Continuation of application No. PCT/EP2020/069550, filed on Jul. 10, 2020.

(30) Foreign Application Priority Data

Jul. 10, 2019 (EP) ..................................... 19185482

(51) Int. Cl.
*A61M 5/158* (2006.01)
*B29C 45/14* (2006.01)
(Continued)

(52) U.S. Cl.
CPC ....... *A61M 5/158* (2013.01); *B29C 45/14065* (2013.01); *B29C 45/7207* (2013.01);
(Continued)

(58) Field of Classification Search
CPC ........ A61M 5/32; A61M 5/34; A61M 5/3293; A61M 2207/00; A61M 3/0279;
(Continued)

(56) References Cited

U.S. PATENT DOCUMENTS 3,029,815 A * 4/1962 Roehr ................... A61M 5/343
29/516
3,961,013 A * 6/1976 Gutlhuber ........... B29C 45/2612
425/577
(Continued)

FOREIGN PATENT DOCUMENTS

DE 3530349 C1 4/1987
EP 3 329 956 A1 6/2018
(Continued)

OTHER PUBLICATIONS

International Search Report and Written Opinion of the International Searching Authority, PCT/EP2020/069550, Sep. 9, 2020, 11 pages.

*Primary Examiner* — Brandy S Lee
*Assistant Examiner* — Antarius S Dan
(74) *Attorney, Agent, or Firm* — Bose McKinney & Evans LLP

(57) ABSTRACT

Disclosed herein is a cannula system including a soft cannula 10 and a cannula holder for holding the soft cannula. The cannula holder has a compressor and a body. The body contains a mounting structure and a cavity for holding a septum. The soft cannula is threaded on the mounting structure. Furthermore, the compressor circumferentially surrounds the mounting structure and at least parts of the body. The compressor provides an internal material tension for exerting a compression force on the soft cannula and the mounting structure.

17 Claims, 3 Drawing Sheets

(51) Int. Cl.
  B29C 45/72 (2006.01)
  B29L 31/00 (2006.01)
(52) U.S. Cl.
  CPC . *A61M 2005/1586* (2013.01); *A61M 2207/00* (2013.01); *B29L 2031/7548* (2013.01)
(58) Field of Classification Search
  CPC .......... A61M 25/0009; A61M 25/0014; A61M 25/0097; A61M 25/0662; B29C 45/14065; B29C 45/7207
  See application file for complete search history.

(56) References Cited

U.S. PATENT DOCUMENTS

| | | | |
|---|---|---|---|
| 4,430,081 | A | 2/1984 | Timmermans |
| 4,781,703 | A | 11/1988 | Walker et al. |
| 4,838,873 | A | 6/1989 | Landskron et al. |
| 6,120,480 | A | 9/2000 | Zhang et al. |
| 8,152,758 | B2 | 4/2012 | Chan et al. |
| 2006/0079848 | A1 | 4/2006 | Pelkey et al. |
| 2014/0350485 | A1* | 11/2014 | Sonderegger ....... B29C 45/1657 604/533 |
| 2017/0135720 | A1 | 5/2017 | Oshida et al. |
| 2019/0160258 | A1* | 5/2019 | Kristen ............. A61M 25/0097 |
| 2019/0275238 | A1* | 9/2019 | Arnold .............. A61M 25/0014 |
| 2021/0393918 | A1 | 12/2021 | Rasmussen et al. |

FOREIGN PATENT DOCUMENTS

| | | | |
|---|---|---|---|
| JP | S 60-144448 | U | 9/1985 |
| JP | 2008-504929 | A | 2/2008 |
| JP | 2017-086566 | A | 5/2017 |
| JP | 2018-166953 | A | 11/2018 |
| WO | WO 99/21605 | A2 | 5/1999 |
| WO | WO 2006/012281 | A1 | 2/2006 |
| WO | WO 2018/033614 | A1 | 2/2018 |
| WO | WO 2018/100072 | A1 | 6/2018 |

* cited by examiner

Figure 2a                    Figure 2b

INJECTION MOLDED CANNULA SYSTEM

RELATED APPLICATIONS

This application is a continuation of PCT/EP2020/069550, filed Jul. 10, 2020, which claims priority to EP 19 185 482.7, filed Jul. 10, 2019, the entire disclosures of both of which are hereby incorporated herein by reference.

BACKGROUND

This disclosure lies in the field of infusion technology. More particularly, it is related to infusion site interfaces and infusion pumps, as well as manufacturing methods for cannula systems for infusion site interfaces.

Infusion pumps are used for parenterally providing patients with liquid medicaments over longer time periods. Nowadays, infusion pumps with very small dimensions are available that can be carried by the patient on the body. Such small-sized ambulatory infusion pumps are particularly useful for metering small doses of highly effective liquid medicaments such as insulin for the treatment of diabetes, or analgesics for pain therapy, which are conveyed through a cannula into the tissue of a patient.

In one approach, an infusion pump, carried somewhere on the body, e.g., attached to a belt, is fluidly connected via flexible tubing to an infusion site interface, also called an insertion head, that is attached to the body of the patient. The infusion site interface comprises a cannula system with a cannula to be inserted into the body tissue, a housing and connector for fluidly connecting the cannula with the flexible tubing connected to the upstream infusion pump. The tubing can be repeatedly connected and disconnected from the infusion site interface. The connector may for example comprise a septum sealingly closing the fluid system of the cannula and housing. The septum can be penetrated by a hollow needle for reversibly establishing a fluid connection. The cannula is preferably made of a flexible material and is thus a soft cannula. Such cannulas are more comfortable for their users, particularly during body movements. Since flexible cannulas cannot be inserted directly into the tissue, an additional piercing device, e.g., in the form of a rigid piercing needle made from metal, is arranged inside the flexible cannula. A pointed end of the piercing device protrudes from the proximal end of the cannula, the cannula end that will be open toward the interstitial fluid. After inserting the piercing device and the stabilized cannula into the body tissue, the rigid piercing device is removed from the flexible cannula. The flexible cannula remains in the body tissue. Generally, a piercing needle is arranged in such a way that it penetrates a septum, which after withdrawal of the piercing needle sealingly closes the distal end of the now open cannula fluid path.

In another approach, the infusion pump device is directly fluidly connected with the infusion site interface. The fluid connection between pump and cannula is established by a hollow connector needle of the pump, reversibly penetrating a septum of the cannula unit that sealingly closes the distal end of the cannula fluid path. Advantageously, the pump can be repeatedly connected and disconnected from the infusion site interface.

In a common method for manufacturing infusion site interfaces with soft and flexible cannulas, a stabilizing pin is introduced in a first step into the flexible cannula, for simplifying the handling of the flexible cannula during the manufacturing process. The temporary structural unit prepared in this manner is inserted into a previously manufactured housing, the flexible cannula and the housing are permanently connected, for example by a thermal process. The stabilizing pin is then drawn out of the flexible cannula, and is replaced by the actual piercing device. The insertion of the piercing devices sometimes damages the flexible cannulas, which results in comparably high rejection rates during manufacturing.

WO 2018/033614 A1 discloses a cannula unit comprising a housing and a flexible cannula. The flexible cannula is provided with an end area that deviates from the shape of the rest of the flexible cannula. The end area of the flexible cannula has for example a funnel-like shape or the shape of a flange. Furthermore, the housing comprises two parts, between which the end area of the flexible cannula is positively locked to the housing by clamping. The two parts of the housing are ultimately connected by welding, particularly laser welding.

Cannula units and systems known in the state of the art suffer from certain drawbacks. For example, if the cannula unit comprises a housing with two parts, which are separately produced and only subsequently connected during the manufacturing process, certain restrictions are imposed. Firstly, the materials have to be suitable for welding or gluing, such that the two housing parts can be connected. Secondly, the connecting step represents an additional step, which increases the manufacturing time and cost of the production. Thirdly, the two parts of the housing must be strictly complementary to each other, thus allowing only minor material tolerances, as otherwise leakage becomes a problem. This is a severe problem in the state of the art, as the amount of deficient products due to non-complementary housing parts is significantly high.

SUMMARY

This disclosure improves the state of the art regarding the design and use of cannula systems in the context of infusion of liquid drugs, thereby avoiding disadvantages of the prior art fully or partly.

In advantageous embodiments, a cannula unit is provided, in which the occurrence of leakage is avoided or at least significantly reduced.

In further favorable embodiments, a cannula unit is provided, which can be manufactured in a time and cost efficient manner.

In additional favorable embodiments, the amount of deficient products during the manufacturing process and thus the rejection rate is reduced.

According to a first aspect of this disclosure, a method is disclosed for manufacturing a cannula system with a body unit and a compressing unit (also referred to herein as a "compressor"). The method comprises providing the body unit (also referred to herein as "body") having a mounting structure, the body unit being mounted onto a molding core pin. Subsequently, a soft cannula is threaded on the mounting structure of the body unit. In a following step, the compressing unit is injection molded on the soft cannula and at least on parts of the body unit. The compressing unit circumferentially surrounds the mounting structure, at least parts of the soft cannula and at least parts of the body unit. Furthermore, the injection-molded compressing unit is cooled, thereby providing an internal material tension of the compressing unit. The cooling typically entails shrinking of the compressing unit. In addition, the molding core pin is removed. It is understood by the skilled person that the molding core pin can be removed either directly after injection molding of the compressing unit, i.e., before cooling of the compressing unit, after cooling the compressing unit or even during cooling of the compressing unit.

Optionally, the body unit is also produced by injection molding. For example, the body unit may be provided by injection molding onto the molding core pin. However, the body unit may also be produced by another suitable method. Particularly, if the body unit is produced by injection molding, the two injection molding steps may be conducted as two separate injection molding steps.

Using injection-molding technology for manufacturing the compressing unit and optionally the body unit has the advantage that only a reduced number of tools is required. Furthermore, no additional connection step such as welding or gluing, is required. In addition, as the compressing unit is injection molded on the body unit and the cannula and subsequently cooled, shrinking induces an internal material tension, which significantly increases the fixture of the soft cannula within the cannula system. The shrinking and the thus associated internal material tension can be increased, if cooling is performed in the mold. Furthermore, injection molding of both the body unit and the compressing unit has the advantage that the two parts are necessarily complementary to each other and thus the amount of material deficient parts is significantly reduced.

It is understood that the term "circumferentially" does not necessarily require that the mounting structure, the cannula and or the body unit have a round cross section and/or a cylindrical shape. These components may independently of each other comprise a round, elliptical or angular cross section and further have any shape suitable for an infusion set.

In some embodiments the compressing unit is injection molded such that it circumferentially surrounds at least ⅓, preferably ½ of the outer surface of the body unit, thereby providing a particular tight and safe connection between the body unit and the compressing unit.

In further embodiments, only a distal end area of the soft cannula is threaded on the mounting structure of the body unit. The compressing unit preferably circumferentially surrounds only the distal end area of the soft cannula. As the skilled person understands, the distal end area is facing away from the patient in an operative state. Thus, the distal end area is closer to the body unit than the proximal end area. Upon insertion into the patient's tissue, the proximal end area is therefore first inserted into the tissue.

In other embodiments, the distal end area is provided with a locking structure for establishing a positive locking (form closure) and/or an adhesive bond between the soft cannula, in particular the distal end area, and the compressing unit. A locking structure (also referred to herein as a "lock") establishing a form lock is advantageous, as during injection molding of the compressing unit on the soft cannula, the material is provided into and/or around the locking structure, thereby providing an improved cannula system, in which the cannula is tightly secured to avoid the cannula separating from the compressing unit and the body unit when the cannula system is withdrawn from the skin. The improved cannula system improves the sealing of the cannula system, thus avoiding the occurrence of leakage of the infusion fluid.

In further embodiments, prior to threading the soft cannula in the mounting structure of the body unit, a locking structure is generated at the distal end area of the soft cannula. The locking structure may be either adhered to the distal end area or a through bore may be generated by drilling. Alternatively, the protruding locking structure such as a nipple may be adhered or welded to the distal end area of the soft cannula.

In some embodiments, the locking structure includes at least one protrusion protruding from the distal end area. For example, the locking structure may be a collar extending from the distal end area of the soft cannula. Preferably, the collar is arranged at the most distal part of the distal end area, i.e., the collar may be a flange. The protrusion may also be a nipple, a hook or a barb. Additionally, or alternatively, the locking structure may be at least one hole. Preferably, the hole is a through bore or a blind hole.

In further embodiments, the distal end area of the soft cannula has a larger diameter than the rest of the cannula before the cannula is threaded on the mounting structure. Thus, the cannula is, when pushed over the mounting structure, not or only slightly laterally expanded, which will result in no or less material creep and potentially leads to less leakage.

In further embodiments, the internal material tension of the compressing unit exerts a compression force which is directed radially inwards. Such a force is particularly advantageous, as the risk of leakage between the cannula and the mounting structure and/or between the cannula and the compressing unit is further decreased.

In some embodiments, the internal material tension of the compressing unit compresses the parts of the soft cannula threaded on the mounting structure. In such embodiments, at least the part of the cannula which is circumferentially surrounded by the compressing unit, preferably the distal end area, is compressed. Thus, the wall thickness of the cannula of this part is smaller than the wall thickness of the rest of the cannula which is not circumferentially surrounded by the compressing unit.

In further embodiments, the body unit and the compressing unit and/or the compressing unit and the soft cannula form a bonded connection during injection molding of the compressing unit.

In some embodiments, the methods may in general consist of two separate injection molding steps, thereby reducing the required amount of manufacturing steps and the overall production time and costs even further.

In a second aspect of this disclosure, a cannula system is disclosed comprising a soft cannula and a cannula unit for holding the soft cannula. The cannula unit comprises or alternatively may also consist of a compressing unit and a body unit, wherein the body unit contains a mounting structure and a cavity for holding a septum. The soft cannula is threaded on the mounting structure of the body unit. Furthermore, the compressing unit circumferentially surrounds the mounting structure and at least parts of the body unit. The compressing unit also comprises an internal material tension for exerting a compression force on the soft cannula and the mounting structure.

For example, such a cannula system may be manufactured by a method as described herein. Furthermore, the body unit and/or the compressing unit are typically injection molded.

In some embodiments, the mounting structure may be a protuberance, in particular a cylindrical or cubical protuberance.

In further embodiments, only a distal end area of the soft cannula is threaded on the mounting structure and the compressing unit circumferentially surrounds the distal end area of the soft cannula.

In some embodiments, the distal end area of the soft cannula comprises a locking structure providing a positive locking and/or an adhesive bond between the soft cannula and the compressing unit. Both form lock and/or an adhesive bond between the soft cannula and the compressing unit provide a tight fit of the compressing unit and the soft cannula, which avoids the occurrence of leakage. A locking structure for establishing positive locking (form closure) between the soft cannula and the compressing unit may be a protruding locking structure or a recessed locking structure. An adhesive bond may for example be provided by attachment of an external adhesive, for example a glue. Such cannula systems of this disclosure provide an improved cannula system, in which the cannula is tightly secured to avoid that the cannula is separated from the compressing unit and the body unit when the cannula system is withdrawn from the skin. The improved cannula system also improves the sealing of the cannula system thus avoiding the occurrence of leakage of the infusion fluid.

In further embodiments the locking structure includes at least one protrusion protruding from the distal end area. For example, the locking structure may be a collar extending from the distal end area of the soft cannula. Preferably, the collar is arranged at the most distal part of the distal end area, i.e., the collar may be a flange. The protrusion may also be a nipple, a hook or a barb. Additionally, or alternatively, the locking structure may be at least one recessed locking structure, such as a hole. Preferably, the hole is a through bore or a blind hole. The locking structure may also be formed by the wall of the soft cannula, in particular by a waved or stepped wall.

In some embodiments, the distal end area of the soft cannula has a larger diameter than the rest of the soft cannula. Thus, in these embodiments, the whole distal area has a larger diameter than the rest of the soft cannula.

Typically, the distal end area of the soft cannula is free of an internal material tension.

In some embodiments, the wall thickness of the distal end area of the soft cannula is smaller than the wall thickness of the rest of the soft cannula.

In other embodiments, the compressing unit compresses at least the distal end area of the soft cannula. In these embodiments, a particular fluid tight system is achieved and the risk of leakage is reduced.

In further embodiments, the body unit and the compressing unit are connected by a bonded connection and/or the soft cannula and the compressing unit are connected by a bonded connection.

It is understood that such a bonded connection is typically only formed by the body unit, the compressing unit and/or the soft cannula itself. Thus, an external adhesive, for example a glue, is neither required nor present, except for embodiments in which adhesive bond between the soft cannula and the compressing unit is provided, for example by a glue.

In some embodiments, the cannula system does not comprise additional connection means, particularly form-lock means, for coupling and/or connecting the compressing unit and the body unit such as for example barbs, nipples, snap fits and the like. The cannula system may also not comprise any additional housing parts or adapters, which are not integral parts of the cannula unit and/or the soft cannula and/or the body unit. Thus, preferred cannula systems may comprise a soft cannula, which is only held in place by the body unit and the compressing unit and consequently not by an additional component not being integral to the body unit or the compressing unit. Thereby, the rejection rate and production effort and cost are reduced.

In further embodiments, the body unit may comprise a septum within the cavity for holding the septum. The septum may be fixed by crimping. Such a septum is typically continuously closed, i.e., free of a slit, prior to insertion of a piercing needle. In particular, such a septum may not comprise a slit elongated in both the lateral and the vertical piercing direction of the septum.

According to another aspect of this disclosure, the cannula system according to any of the embodiments described herein can be used in an infusion set.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIGS. 2a to 2c schematically show the manufacturing method of a cannula system according to an embodiment of this disclosure;

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
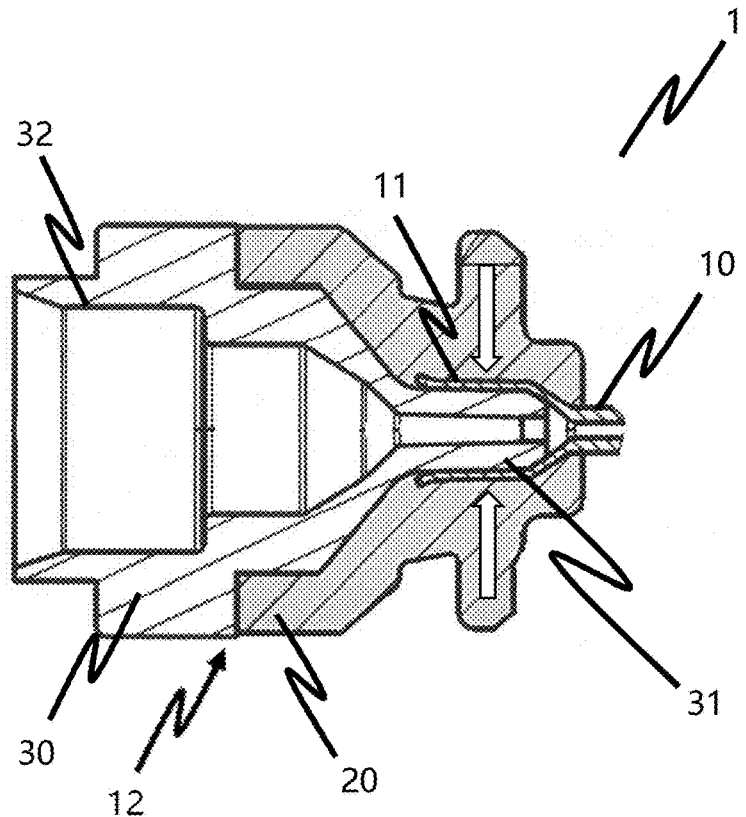
FIG. 1 shows a cross-sectional view of a cannula system in accordance to an embodiment of this disclosure.

FIG. 1 shows an advantageous embodiment of a cannula system 1 according to this disclosure. Cannula system 1 comprises soft cannula 10 and a cannula unit (also referred to herein as a "cannula holder") 12 for holding soft cannula 10. The cannula holder includes compressing unit ("compressor") 20 and body unit ("body") 30. Body 30 further comprises mounting structure 31 and cavity 32 for receiving a septum. Distal part 11 of soft cannula 10 is threaded on mounting structure 31. The diameter of distal end area 11 of soft cannula 10 is larger than the diameter of the rest of the soft cannula. Compressor 20 circumferentially surrounds distal end area 11 of soft cannula 10, mounting structure 31 and also an additional part of body 30. As shown in FIG. 1, more than ⅓ of the outer surface of the body are circumferentially surrounded by compressor 20.

As indicated by the arrows, the compressor 20 has an internal material tension, thereby exerting a radially inwards directed compression force on the distal end area of the soft cannula and the mounting structure. As a result, a particular tight connection between soft cannula 10, mounting structure 31 and compressor 20 is achieved. Furthermore, as can be readily seen in FIG. 1, the wall thickness of distal end area 11 of soft cannula 10 is smaller than the wall thickness of the rest of soft cannula 10. In addition, as indicated by the arrows, distal end area 11 of soft cannula 10 is compressed by the compression force exerted by compressor 20. Compressor 20 and body 30 are connected by a bonding connection at their contact area. As a result, a reliable and sealingly tight connection is established.

Figure 2C:
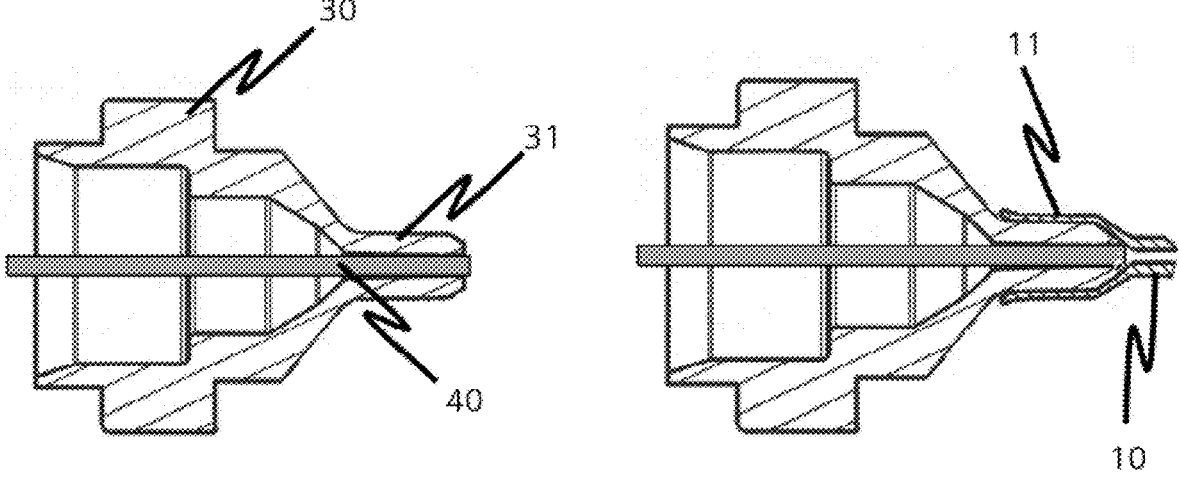
Figure 2C:
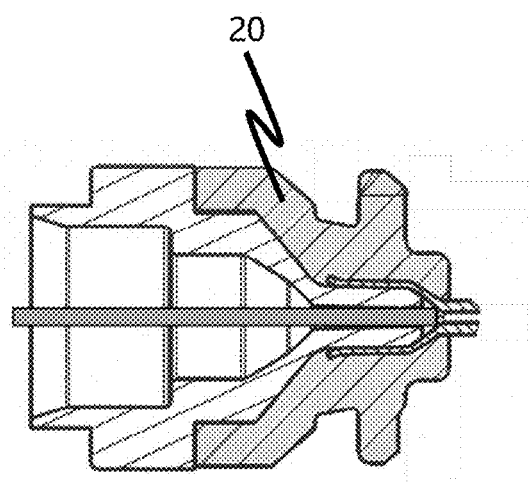

FIGS. 2a to 2c depict certain steps of a method of manufacturing a cannula system according to an advantageous embodiment of this disclosure. As shown in FIG. 2a, body 30 with mounting structure 31 is injection molded onto a molding core pin 40 (mold not shown). In a following step, distal end area 11 of soft cannula 10 is threaded on mounting structure 31 (FIG. 2b). Afterwards, compressor 20 is injection molded on the distal end area of the soft cannula, on the mounting structure and also on further parts of body 30 (FIG. 2*c*, mold not shown). As the compressor is at least partially injection molded on body 30, any production imprecision of the proximal face of the body unit is less relevant, as the compressor is necessarily complementary to those parts of the body 30. Once compressor has been injection molded, molding core pin 40 can be removed and the compressor can be cooled, upon which an internal material tension is established, thereby exerting a force on distal end area 11 of soft cannula 10 and mounting structure 31. Generally, the cooling can be performed in the mold and/or the cooling may be achieved by active cooling. Thus, the compressor is not allowed to cool to room temperature by itself, but actively cooled, particularly by using a cooling medium. Such rapid cooling enhances the internal material tension. The two-step injection molding sequence can be performed significantly faster than the methods for manufacturing cannula unit as known in the state of the art.

Figure 3:
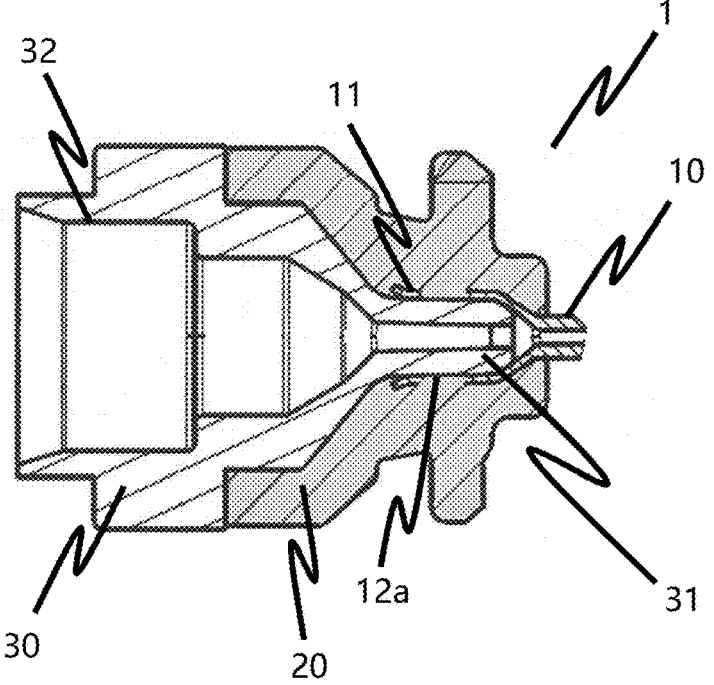
FIG. 3 shows a cross-sectional view of a cannula system in accordance to another embodiment of this disclosure.

FIG. 3 shows another advantageous embodiment of a cannula system 1 according to this disclosure. Cannula system 1 comprises soft cannula 10 and a cannula unit containing compressor 20 and body 30. Body 30 comprises mounting structure 31 on which distal end area 11 of the soft cannula 10 is threaded. In the particular embodiment shown, distal end area 11 comprises two holes 12*a* as locking structures, which are provided as through bores. The dimension of holes 12*a* are drawn in exaggeration for demonstrative purposes only. Even though the arrows indicating the compressing force are not shown in FIG. 3 (see FIG. 1), also in this embodiment with holes 12*a*, a compressing force is exerted by the compressor on soft cannula 10. As can be seen, parts of the compressor 20 enter holes 12*a* during injection molding. After the compressor is cooled, a tighter sealing between compressor 20 and soft cannula 10 is achieved. Additionally, the fixation of soft cannula 10 within thin cannula system is improved.

Figure 4:
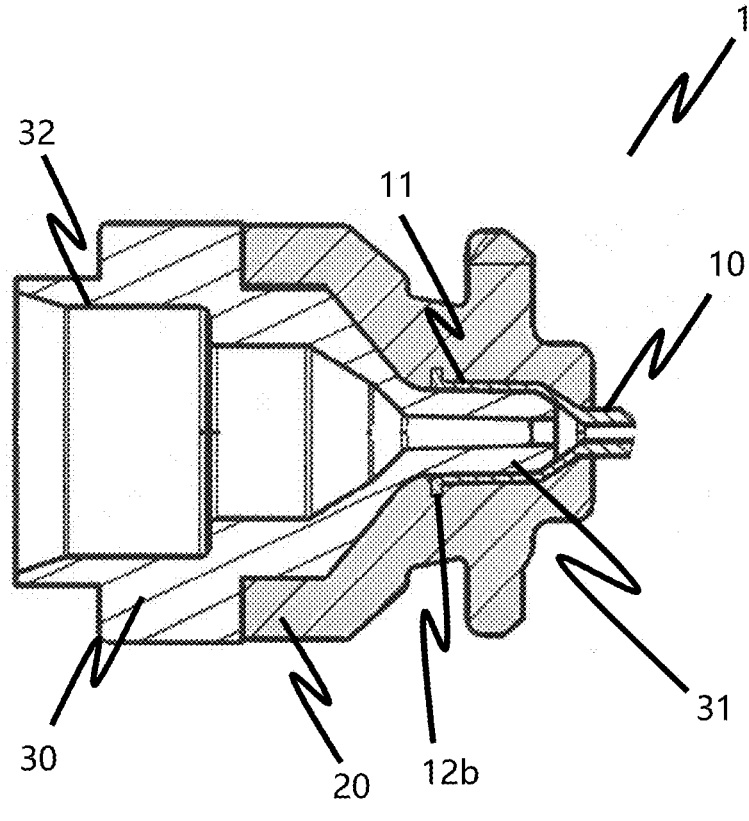
FIG. 4 shows a cross-sectional view of a cannula system in accordance to another embodiment of this disclosure.

FIG. 4 depicts another embodiment of cannula system 1, with soft cannula 10 and a cannula unit comprising compressor 20 and body 30 with mounting structure 31. In general, the mounting structure may be a protrusion of the body, such as a nipple. Distal end area 11 of soft cannula 10 comprises collar 12*b* as a locking structure or lock, which establishes a form lock between soft cannula 10 and compressor 20. Collar 12*b* is circumferentially arranged at the most distal part of distal end area 11. During injection molding of compressor 20, the material is provided around collar 12*b*. As a result, soft cannula 11 is anchored within compressor 20, thereby both increasing fixation of the cannula within the cannula system and the sealing between the cannula and the compressor.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for manufacturing a cannula system, the method comprising:
   providing a body having a mounting structure, the body being mounted onto a molding core pin and wherein the body is provided by injection molding the body onto the molding core pin;

positioning a soft cannula on the mounting structure;
   injection molding a compressor on the soft cannula and at least part of the body, wherein the compressor circumferentially surrounds the mounting structure, at least part of the soft cannula and the at least part of the body, wherein the compressor is complementary to and forms a tight connection with the at least part of the body where the compressor is molded on the body, and wherein the compressor and the body and the compressor and the soft cannula form bonded connections during injection molding of the compressor;
   actively cooling the compressor and thereby providing an internal material tension of the compressor; and
   removing the molding core pin.

2. The method according to claim 1, wherein only a distal end area of the soft cannula is positioned on the mounting structure of the body.

3. The method according to claim 2, wherein the distal end area of the soft cannula is provided with a lock for establishing a form lock and/or an adhesive bond between the soft cannula and the compressor.

4. The method according to claim 3, wherein, prior to positioning the soft cannula on the mounting structure of the body, the lock is generated at the distal end area of the soft cannula.

5. The method according to claim 3, wherein the lock includes at least one protrusion.

6. The method according to claim 5, wherein the lock is selected from the group consisting of (i) a protruding collar arranged at the most distal part of the distal end area and (ii) a protrusion on the compressor extending through at least one hole in the soft cannula.

7. The method according to claim 6, wherein the lock includes the protrusion on the compressor extending through the at least one hole in the soft cannula to thereby improve a seal between the compressor and the soft cannula.

8. The method according to claim 2, wherein the distal end area of the soft cannula has a larger diameter than the rest of the cannula before the cannula is positioned on the mounting structure.

9. The method according to claim 2, wherein the compressor circumferentially surrounds only the distal end area of the soft cannula.

10. The method according to claim 1, wherein the internal material tension of the compressor exerts a radially inward compression force and/or wherein the internal material tension of the compressor compresses the soft cannula.

11. The method according to claim 1, wherein the distal end area of the soft cannula has a larger diameter than the rest of the soft cannula.

12. The method according to claim 1, wherein the compressor compresses at least the distal end area of the soft cannula and/or wherein the body and the compressor are connected by a bonded connection and/or wherein the soft cannula and the compressor are connected by a bonded connection.

13. A method of using an infusion set, comprising:
   providing a cannula system according to claim 1; and
   using the cannula system in the infusion set.

14. The method for manufacturing a cannula system according to claim 1, wherein the body is provided by injection molding onto the molding core pin.

15. The method for manufacturing a cannula system according to claim 1, wherein the compressor shrinks from the active cooling of the compressor.

16. The method for manufacturing a cannula system according to claim 1, wherein the active cooling of the compressor includes using a cooling medium.

17. The method for manufacturing a cannula system according to claim 16, wherein the active cooling of the compressor is performed in a mold.

* * * * *